United States Patent [19]
Absten

[11] Patent Number: 5,246,419
[45] Date of Patent: Sep. 21, 1993

[54] INTRA-ABDOMINAL INSUFFLATION APPARATUS

[75] Inventor: Gregory T. Absten, Grove City, Ohio
[73] Assignee: Omnivision, Inc., Columbus, Ohio
[21] Appl. No.: 941,318
[22] Filed: Sep. 4, 1992
[51] Int. Cl.$^5$ ............................................. A61M 13/00
[52] U.S. Cl. ........................................ 604/26; 128/747
[58] Field of Search ................................. 604/23–26; 128/747, 748

[56] References Cited

U.S. PATENT DOCUMENTS

| | | | |
|---|---|---|---|
| 3,858,572 | 1/1975 | Binard et al. | 128/747 |
| 4,048,992 | 9/1977 | Lindemann et al. | 604/26 |
| 4,193,406 | 3/1980 | Jinotti | 604/26 |
| 4,464,169 | 8/1984 | Semm | 604/26 |
| 4,648,386 | 3/1987 | Morritt et al. | 604/26 |
| 4,676,774 | 6/1987 | Semm et al. | 604/26 |
| 4,735,603 | 4/1988 | Goodson et al. | 604/26 |
| 4,874,362 | 10/1989 | Wiest et al. | 604/26 |
| 4,966,578 | 10/1990 | Baier et al. | 604/26 |
| 5,002,557 | 3/1991 | Hasson | 604/26 |
| 5,006,109 | 4/1991 | Douglas et al. | 604/26 |
| 5,013,294 | 5/1991 | Baier | 604/26 |
| 5,152,745 | 10/1992 | Steiner et al. | 604/26 |

FOREIGN PATENT DOCUMENTS 2303512 10/1976 France ..................... 604/26

Primary Examiner—Ralph Lewis
Attorney, Agent, or Firm—George Wolken, Jr.

[57] ABSTRACT

The present invention consists of an apparatus for supplying insufflation gas at high flow rates during laparoscopic surgery including some or all of the following features: at least two gas delivery tubes; a pressure-sensing transducer independent of the gas flow in any gas delivery tube, said pressure sensor being connected to the gas delivery system to decrease gas flow automatically if over pressurization occurs and to increase flow rates if under pressurization occurs; an automatic valve to switch at least one of said gas delivery tubes to a suction tube if serious over pressurization is sensed; manual controls for suction and flow rates to allow the operator manually to flush rapidly with insufflation gas upon direction of the surgeon; gas quality control devices including filtration means, humidification means, temperature controlling means, and means for adding medication or other chemicals to the insufflation gas stream, typically with a nebulizer.

7 Claims, 3 Drawing Sheets

INTRA-ABDOMINAL INSUFFLATION APPARATUS

FIELD OF THE INVENTION

The present invention relates to the general field of medical devices. More particularly, the present invention relates to a medical device for use during laparoscopic surgery to maintain positive gas pressurization of the abdominal cavity, enabling thereby better access for examination, diagnosis and treatment.

BACKGROUND OF THE INVENTION

A dominant feature of modern surgical procedures is to minimize the size of the region within the patient affected by the surgery. Such "minimally invasive" surgery has led to major growth in surgical procedures performed through various types of endoscopes. Previously, surgery was dominated by open surgical procedures in which the surgeon opens the region of the patient requiring attention, and carries out the procedure directed by his or her direct viewing of the surgical field. Recent advances in optics, laser surgery, electrosurgery, as well as miniaturized manipulation techniques have opened up a radically new approach and added significantly to the range of procedures the surgeon can call upon in treating the patient. More and more, the surgeon will place a few small incisions into the patient, and insert therein various viewing and surgical devices. Typically in such procedures, the surgical field will be illuminated and viewed by means of optical fiber devices inserted into the patient. The surgery is then performed by means of miniature devices also inserted through such small incisions, while the surgeon observes and guides the interaction of tissue and instruments on a television monitor.

Such endoscopic surgical procedures are becoming standard in general surgery, gynecology, thoracic surgery, orthopedic surgery, pulmonary medicine, gastroenterology, and are developing rapidly in neurosurgery, spinal surgery and other areas. This trend towards endoscopic surgery has been especially dominant in abdominal surgery, in which the abdominal cavity provides ample opportunity for surgery through an endoscope (typically referred to as a "laparoscope" when used in the abdominal cavity, and the procedures performed through the laparoscope are referred to as "laparoscopy".). Among the procedures commonly performed by abdominal laparoscopy are gall bladder removal, hernia repair, appendectomy, bowel resection, hysterectomy, removal of ectopic pregnancies, and others.

However, laparoscopic abdominal surgery is hindered by the confined space within the abdominal cavity in which to manipulate tissues and instruments. In conventional, open surgery, the various organs can typically be moved about to provide better viewing of the surgical field and better access for the surgeon. This is not convenient in laparoscopic surgery and alternative ways to operate in confined body cavities must be developed.

The preferred technique at the present time is to inflate the abdominal cavity with a suitable gas, maintaining a positive gas pressure to inflate the abdominal cavity in a manner not too dissimilar to a balloon. Such pneumoperitoneum provides additional working area for the surgeon, allowing instruments to be manipulated in the abdominal cavity with less obstruction. The thrust of the present invention is to describe an improved instrument for insufflation of the abdominal cavity for the purpose of maintaining pneumoperitoneum during laparoscopy.

Conventional insufflation suffers from several disadvantages. Perhaps the most serious disadvantage is the relatively low flow rates of gas: typically of the order of 6–15 liters per min. (l/m). As more incisions are used in laparoscopy, leakage becomes a more serious problem and the maintenance of pneumoperitoneum becomes difficult or impossible. This is exacerbated in certain gynecological procedures in which a direct escape path for gas through the patients vagina becomes available. A particular problem is created when laser or electrosurgery create significant amounts of smoke during the procedure. High suction rates are required to remove such smoke from the patient. The typical insufflator is unable to compensate and the patient's abdomen deflates.

Increasing the flow rates of insufflation gas would help in the maintenance of pneumoperitoneum, but increases the dangers to the patient of over pressurization. It is an important object of the present invention to provide high-flow rate insufflation (typically 10–40 l/m) with over pressurization safety measures.

Another problem with conventional insufflation is the quality of the insufflation gas delivered to the patient. Carbon dioxide is the typical insufflation gas. But carbon dioxide reacts with the abdominal fluids to create small amounts of carbonic acid, increasing postoperative discomfort for the patient. Also, the delivery of cold, dry insufflation gas to the patient tends to desiccate the serosa of intra-abdominal cavity structures, increasing the possiblity of intra-abdominal adhesions. The apparatus of the present invention addresses these particular problems with conventional insufflation as well as providing for high flow rate insufflation in a safe manner.

SUMMARY OF THE INVENTION

The present invention consists of an apparatus for supplying insufflation gas at high flow rates during laparoscopic surgery including some or all of the following features: at least two gas delivery tubes; a pressure-sensing transducer independent of the gas flow in any gas delivery tube, said pressure sensor being connected to the gas delivery system to decrease gas flow automatically if over pressurization occurs; an automatic valve to switch at least one of said gas delivery tubes to a suction tube if serious over pressurization is sensed; gas quality control devices including filtration means, humidification means, temperature controlling means, and means for adding medication or other chemicals to the insufflation gas stream, typically with a nebulizer.

OBJECTS OF THE INVENTION

A primary object of the present invention is to supply insufflation gas to the patient at high flow rates.

Another object of the present invention is to provide for pressure sensing independent of the gas flow in any gas delivery tube.

Yet another object of the present invention is to provide for automatic decrease in the flow of insufflation gas if over pressurization is sensed.

Another object of the present invention is to provide automatic suction for active removal of insufflation gas from the patient if over pressurization occurs.

Another object of the present invention is to provide for in-line filtration, humidification and temperature control of the insufflation gas.

Yet another object of the present invention is to provide means for adding medication or other chemicals to the insufflation gas stream.

Another object of the present invention is to provide for cascaded tanks of insufflation gas, resulting in uninterrupted gas flow when a single tank becomes exhausted.

DESCRIPTION OF PREFERRED EMBODIMENTS

Figure 1:
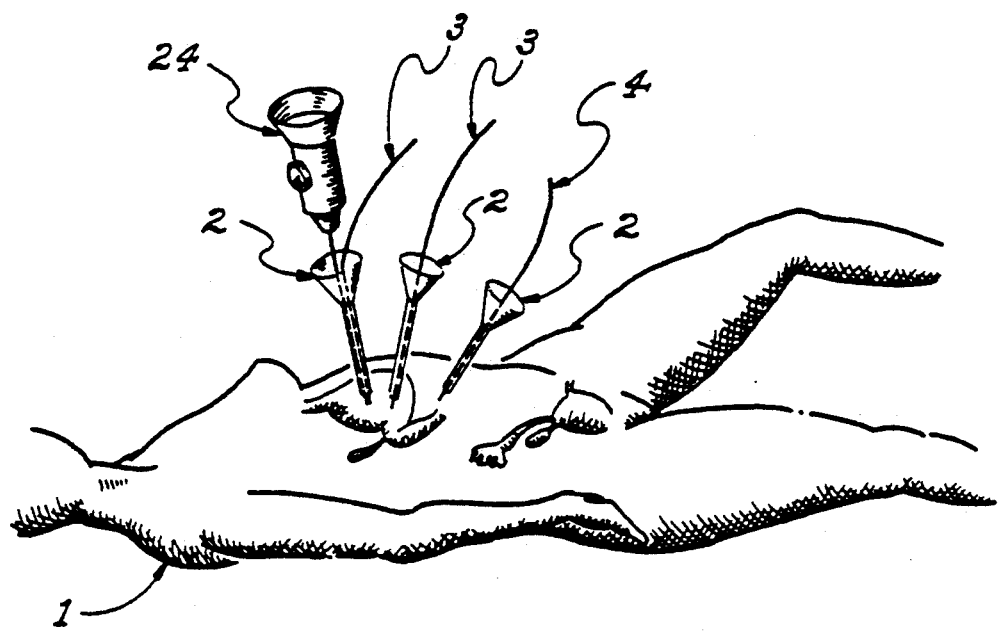
FIG. 1: Partial cut-away view of typical laparoscopic operation in progress.

FIG. 1 shows a typical laparoscopic operation in progress on patient, 1, using three incisions and means of access, 2, into the patient's abdominal cavity. Normal surgical procedure involves piercing the abdomen with a sharp instrument ("trocar") surrounded by a sleeve or cannula. Following piercing of the abdomen, the trocar is removed, leaving the cannula, 2, through which instruments are inserted. The cannula, 2, typically would have a port on the side for insufflation. However, the present invention is not related to the particular structure of trocar or cannula, and a generic access port into the patient's abdomen is shown as 2 in FIG. 1.

In typical laparoscopic procedures, at least one of the incisions will typically be used for insertion of a laparoscope, 24. The laparoscope, 24, will typically be used for viewing, manipulation, tissue removal, or any of numerous other surgical procedures carried out by means of laparoscopes. The detailed instrumentation for such procedures are not central to the present invention and are not shown in FIG. 1.

FIG. 1 shows three incisions for the particular surgical procedure. This is intended merely for illustration as anywhere from two to five incisions are commonly employed in modern laparoscopy. An important feature of the present invention is the high flow rates of insufflation gas employed; sufficient to compensate for loss of insufflation gas due to additional incisions, active smoke evacuation and suction, and other sources of leakage. Typically, each gas pathway, 3 would carry at least 6-15 l/m of insufflation gas as is typical in conventional insufflation. The use of multiple ports for delivery of insufflation gas to the patient, as in the present invention, increases the quantity of deliverable gas without requiring excessive flow rates, pressures or tube size through any single cannula.

Also shown in FIG. 1 are the connections to the insufflator, 3 and 4. For the particular embodiment described herein, 3 denotes tubes delivering insufflation gas to the patient while 4 denotes a pressure-sensing transducer for sensing the pressure in the abdominal cavity independent of the flow of gas in each line. Pressure sensor 4, can be of any convenient type. We presently envision sensor 4 to be merely a hollow piece of tubing connecting the interior of the abdominal cavity to an external pressure-measuring transducer (not shown in FIG. 1). However, sensor 4 could also be a sealed tube sensing directly the pressure or a miniature pressure sensor itself directly inserted into the abdominal cavity. For the purposes of the present invention, the precise form of the pressure sensor is not critical, and we use "pressure sensor" to denote any such device.

Pressure sensor 4 need not occupy an incision separate from the incisions carrying the inflowing insufflation gas. It is very feasible for the pressure sensor, 4 to be inserted into the patient through one of the incisions also carrying a gas delivery tube, 3. However, unlike the conventional insufflators, the present invention uses direct measurement of pressure in the abdominal cavity unencumbered by gas flows through tubing 3 which would affect the accuracy of any pressure measurement. Therefore, it is important to the practice of the present invention that the pressure sensor of line 4 be physically distinct from the gas delivery tubes, 3. Conventional insufflation estimates gas pressure in the patient's abdominal cavity by means of pressure gauges measuring the pressure in gas flow lines, 3. The present invention improves on this inexact method by means of a separate pressure sensor in a separate location attached to a separate line, 4. When using high rates of flow of insufflation gas, as in the present invention, it becomes important to monitor accurately the pressure in the patient. This is the function of sensor 4.

Figure 2:
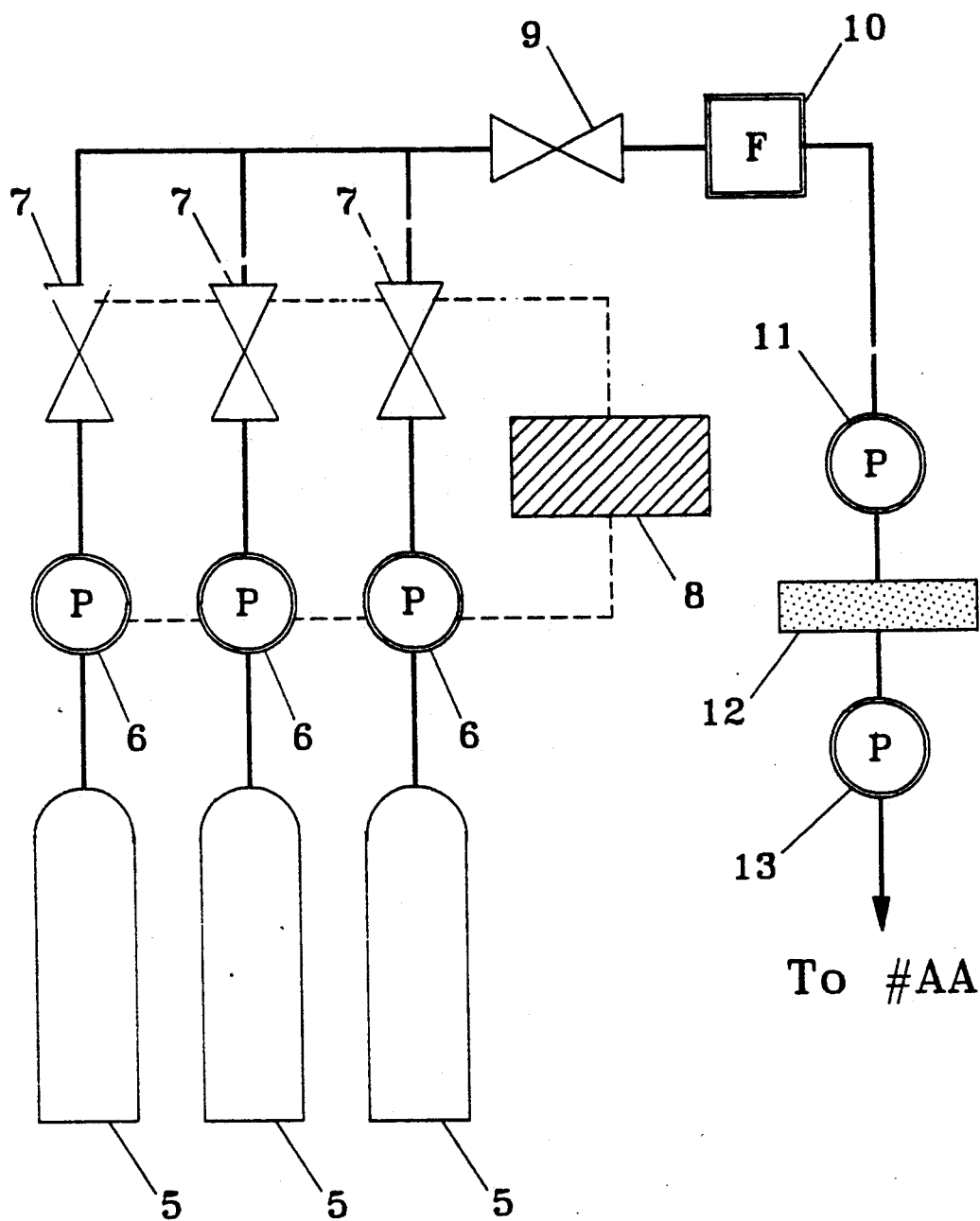
FIG. 2: Schematic drawing of insufflation gas supply system.
Figure 3:
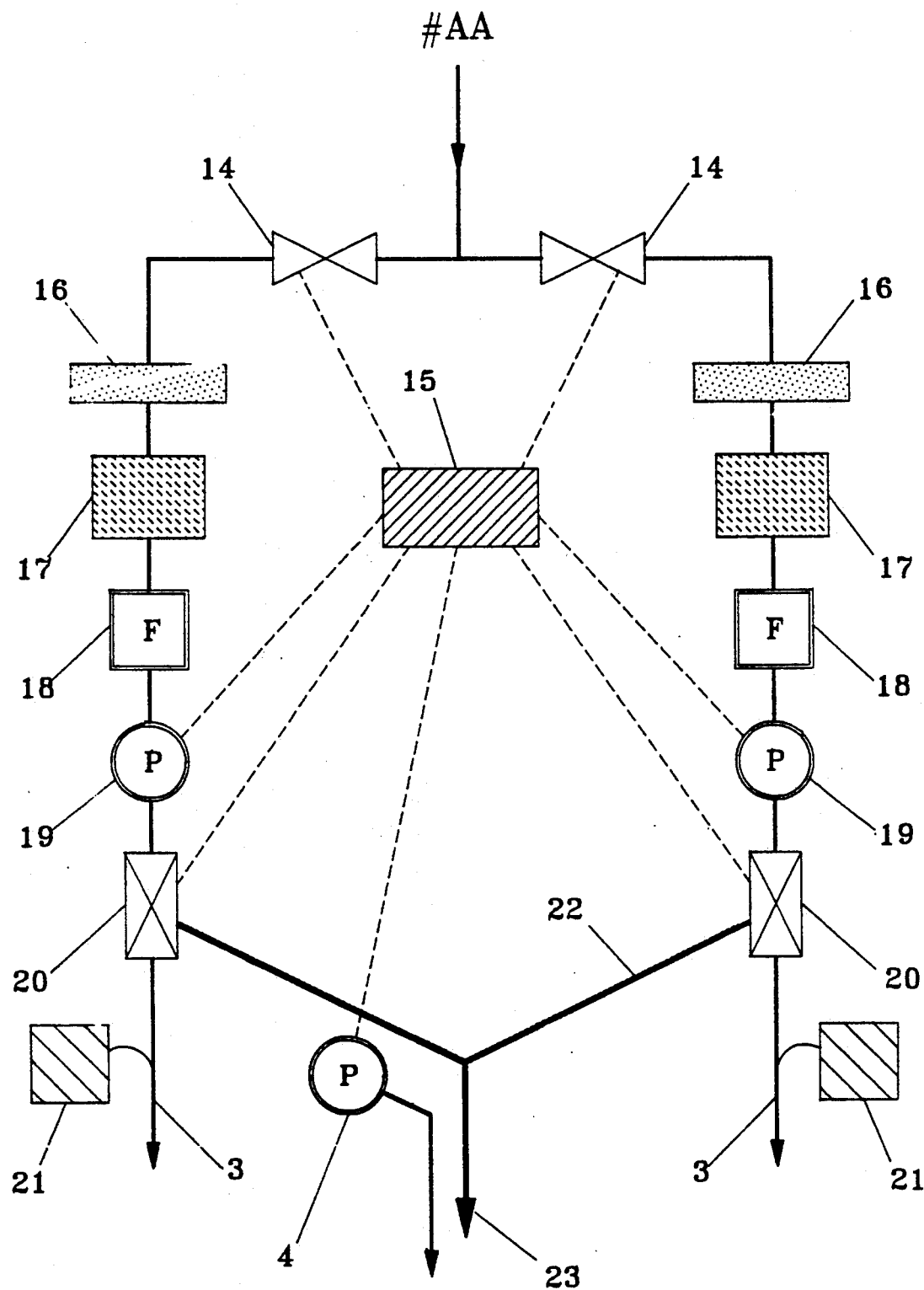
FIG. 3: Schematic drawing of insufflation gas delivery and control system.

FIGS. 2 and 3 show a schematic view of the preferred method of insufflation according to the present invention. In FIG. 2 we concentrate on the gas delivery and control system in the region near the supply of gas. FIG. 3 shows the region and control system for delivery of gas to the patient. The embodiment of the present invention is best understood by a step-by-step illustration of the gas flow to the patient and the control system regulating such flow.

FIG. 2 shows as 5 a supply of insufflation gas, typically carbon dioxide although other insufflation gas, such as nitrous oxide, can also be used. For the present instance we illustrate the case in which the supply of gas is from cylinders, 5. It is important in such a case that there be no interruption of gas supply during the surgical procedure, with the attendant delay and increase of the patient's time under anesthesia. Therefore, the present insufflation apparatus envisions pressure sensors, 6 and valves, 7 located in each gas line emanating from a plurality of gas cylinders, 5. A microprocessor, 8 will typically be used to monitor the pressure in each gas line and turn on additional cylinders sequentially as the gas becomes exhausted in the previously-used cylinder.

The overall gas line to the patient would typically contain a shut-off valve, 9, a flow meter, 10, and a pressure gauge, 11. The flow and pressure information would typically be displayed for the operating room technician to monitor the overall insufflation process.

If the operating room has a delivered supply of insufflation gas through a wall valve, such gas can be delivered directly to valve 9 in an alternative embodiment of the present invention. In such cases, gas cylinders, 5, gauges, 6, valves, 7 and microprocessor 8 can be eliminated.

In typical operation, the apparatus of the present invention would contain a filter, 12 to remove any impurities, dust, or small particles from the gas flow. Also, the typical apparatus of the present invention would have an additional pressure gauge, 13, positioned downstream from pressure gauge 11. Use of these two gauges in combination would give the technician a reading of the pressure drop across the filter, 12. Recognizing that an abnormally large pressure drop indicates excessive clogging of filter, 12, gauges 11 and 13 provide information required to change filter 12 at the appropriate time for maintaining clean insufflation gas without wasting service life by prematurely discarding such filters.

FIG. 3 is a continuation of the insufflation apparatus, gas flow, and control system begun in FIG. 2. We show in FIG. 3 two separate gas delivery paths, 3, for bringing insufflation gas to the patient. More than two separate paths could be used. If more than two separate gas delivery paths are employed, each would typically be duplicates of the sort shown in FIG. 3. Also, FIG. 3 shows each gas delivery path having identical features for controlling and processing the insufflation gas. Typically, this is envisioned to be the case, although in certain cases (adding of medication, for example) it may not be required for every path for insufflation gas to have the same equipment as every other path.

Typical pathways for delivering insufflation gas to the patient would have a flow controlling valve, 14 connected to a microprocessor 15. In addition, each insufflation gas pathway would typically contain a filter, 16, a means to control the temperature and humidity of the insufflation gas, 17, flow meter, 18, and pressure gauge 19. Such controls need not all be used in any particular apparatus, or may take the form of an internal "alarm" in which pressure (for example) would be measured but not displayed for the operator unless problems are detected.

An important feature of the present invention is pressure sensor 4, independent of every gas-delivery pathway and directly measuring the pressure in the patient. In typical operation, pressure sensor, 4, would be connected to microprocessor 15 to automatically reduce the flow of insufflation gas through valves 14 when a predetermined limit is exceeded. In addition, microprocessor 15 would typically be programmed to increase gas flow through valves 14 when (due to removal of instruments, opening of another incision, etc.) the pressure in the patient measured by gauge 4 falls below a predetermined value.

Typically, microprocessor 15 would be attached pressure gauges 19 in addition to pressure gauge 4, should a defective valve 14 become stuck in its open position, the pressure in gauge 19 would give such information to the processor 15 enabling corrective actions to be taken on the proper gas pathway.

The present insufflation apparatus has the capability to apply active suction as an additional safety feature. The present apparatus is intended to use very high rates of flow of insufflation gas: up to about 40 l/m. If over pressurization occurs with such high flow rates, it may be insufficient to merely reduce incoming flow of insufflation gas by means of valves 14. It may also be necessary to provide active evacuation of the body cavity by the application of suction. This is accomplished by means of valve 20, typically a venturi-type tube and valve, connected by tubing 22 to a source of suction (not shown) 23. Suction is commonly available during surgical procedures and no separate source of suction for the insufflation apparatus of the present invention in envisioned. Microprocessor 15 would typically be programmed with at least two separate "alarm points" the first of which triggering reduction of flow by means of valves, 14 and the second of which triggering active suction by activation of 22. (FIG. 3 shows suction applied equally to both gas pathways. In practice, it may be sufficient to apply suction only to one pathway while reducing flow in the other.)

When laser or electrosurgery is employed, typically large amounts of smoke would be generated. Removal of such smoke requires active suction. In addition to the suction tubes used specifically for smoke removal, the present apparatus can also be employed to assist in this task. High flow rate insufflation, as in the present apparatus, coupled with active suction by means of 23 can be used as a flushing means to purge the abdominal cavity of smoke more quickly than conventional suction. An additional feature of the present invention would allow the operator manually to activate suction, 23, while continuing high rates of insufflation in other tubes. This would allow rapid flushing of undesired gases from the abdominal cavity. Manual activation of suction should not override the monitoring and control systems directed by microprocessor, 15, as this would negate several of the safety features of the present invention which are important for patient safety.

In addition to the above features, a typical insufflation apparatus of the present invention could contain a nebulizer (or similar device), 21 for the introduction of medication into the gas stream. Each gas line is shown in FIG. 3 as having its own nebulizer although this may not be necessary in practice.

I claim:

1. An apparatus for delivering insufflation gas to a patient comprising:
   a) a plurality of gas delivery tubes for connecting, in parallel, the source of said insufflation gas with an interior body cavity of said patient through a plurality of parallel inlets into said body cavity, and
   b) a means for measuring the insufflation pressure in said body cavity separate from the flow of gas in each of said gas delivery tubes, and
   c) a plurality of means for controlling the flow of said insufflation gas connected to said pressure-sensing means, automatically adjusting said flow independently in each of said gas delivery tubes to compensate for aberrant insufflation pressure.

2. An apparatus as in claim 1 wherein said gas delivery tubes have a total gas flow capacity in the range of 10 to 40 liters per minute.

3. An apparatus as in claim 1 further comprising:
   a') a source of suction connected to at least one of said gas delivery tubes, and
   b') a means for connecting either insufflation gas or suction to said tube in response to the pressure in said body cavity.

4. An apparatus as in claim 3 wherein said connecting means is manually activated for rapid cavity flushing with insufflation gas.

5. An apparatus as in claim 1 further comprising means for controlling the temperature of said insufflation gas independently in each of said gas delivery tubes.

6. An apparatus as in claim 1 further comprising means for controlling the humidity of said insufflation gas independently in each of said gas delivery tubes.

7. An apparatus as in claim 1 further comprising means for adding medications to said insufflation gas independently in each of said gas delivery tubes.

* * * * *